(12) United States Patent
Richiardi et al.

(10) Patent No.: US 10,740,655 B2
(45) Date of Patent: Aug. 11, 2020

(54) INTEGRATIVE PREDICTION OF A COGNITIVE EVOLUTION OF A SUBJECT

(71) Applicants: CENTRE HOSPITALIER UNIVERSITAIRE VAUDOIS, Lausanne (CH); SIEMENS HEALTHCARE GMBH, Erlangen (DE)

(72) Inventors: Jonas Richiardi, Geneva (CH); Tobias Kober, Lausanne (CH); Julius Popp, Lausanne (CH)

(73) Assignees: Centre Hospitalier Universitaire Vaudois, Lausanne (CH); Siemens Healthcare GmbH, Erlangen (DE)

( * ) Notice: Subject to any disclaimer, the term of this patent is extended or adjusted under 35 U.S.C. 154(b) by 91 days.

(21) Appl. No.: 16/025,536

(22) Filed: Jul. 2, 2018

(65) Prior Publication Data

US 2020/0005095 A1   Jan. 2, 2020

(51) Int. Cl.
*G06K 9/62* (2006.01)
*G16H 30/20* (2018.01)
(Continued)

(52) U.S. Cl.
CPC .......... *G06K 9/6267* (2013.01); *A61B 5/0042* (2013.01); *A61B 5/055* (2013.01);
(Continued)

(58) Field of Classification Search
CPC .... G06K 9/6267; G06K 9/6262; G16H 50/30; G06N 20/00; A61B 5/0042; A61B 5/055;
(Continued)

(56) References Cited

U.S. PATENT DOCUMENTS

| 2004/0166536 A1* | 8/2004 | Kerkman | A61B 5/16 435/7.2 |
| 2009/0022825 A1* | 1/2009 | Kerkman | A61B 5/16 424/752 |

(Continued)

OTHER PUBLICATIONS

Elaheh Moradi et al., Machine learning framework for early MRI-based Alzheimer's conversion prediction in MCI subjects, 2015, NeuroImage 104, p. 398-412. (Year: 2015).*

(Continued)

*Primary Examiner* — Brenda C Bernardi
(74) *Attorney, Agent, or Firm* — Laurence Greenberg; Werner Stemer; Ralph Locher

(57) ABSTRACT

A system and method automatically predicts an evolution of a cognitive score for a subject by classifying a cognitive data set for the subject into a first or second class by determining the cognitive set of data for each subject of a group, acquiring for each subject a neuropsychological score used for classifying each subject in the first or second class, and training a two-class machine learning classification algorithm on the cognitive data sets of all subjects. For each subject, the cognitive data set is used as input of the algorithm and the obtained classification of the subject as output target of the algorithm. The algorithm classifies each cognitive data set in the first or second class. The evolution of the cognitive score of a subject is predicted by the trained algorithm for automatically classifying a new cognitive dataset for the subject into the first or second class.

11 Claims, 2 Drawing Sheets

(51) Int. Cl.
  *G16H 50/30*   (2018.01)
  *A61B 5/055*   (2006.01)
  *A61B 5/00*    (2006.01)
  *G06N 20/00*   (2019.01)

(52) U.S. Cl.
  CPC .......... *A61B 5/4088* (2013.01); *A61B 5/7267* (2013.01); *G06K 9/6262* (2013.01); *G06N 20/00* (2019.01); *G16H 30/20* (2018.01); *G16H 50/30* (2018.01); *A61B 2576/026* (2013.01)

(58) Field of Classification Search
  CPC ................ A61B 5/4088; A61B 5/7267; A61B 2576/026
  See application file for complete search history.

(56) References Cited

U.S. PATENT DOCUMENTS

| | | | | |
|---|---|---|---|---|
| 2011/0182820 A1* | 7/2011 | Seeburger | .......... | G01N 33/6896 424/9.2 |
| 2019/0272922 A1* | 9/2019 | Albright | ................ | G16H 50/50 |

OTHER PUBLICATIONS

Alexander Schmidt-Richberg et al., Learning Biomarker Models for Progression Estimation of Alzheimer's Disease, 2016, PLoS One 11(4), p. 1-33. (Year: 2016).*

S L Miller et al., Hippocampal activation in adults with mild cognitive impairment predicts subsequent cognitive decline, Jun. 2008, Journal of Neurology, Neurosurgery, and Psychiatry, 79(6), p. 630-635. (Year: 2008).*

Valeria Kebets: "Functional Imaging Markers of the MCI Brain in Task and at Rest: Detecting Memory and Connectivity Impairments in Prodromal Alzheimer's Disease" Thesis No. 189 Université de Genève, 2016.

Micheal Ewers et al., "Prediction of conversion from mild cognitive impairment to Alzheimer's disease dementia based upon biomarkers and neuropsychological test performance." Neurobiology of Aging 33 (2012) pp. 1203-1214.

Stefan J. Teipel et al.: "Multivariate deformation-based analysis of brain atrophy to predict Alzheimer's disease in mild cognitive impairment", NeuroImage 38 (2007) pp. 13-24, Available online Jul. 18, 2007.

K.M. Gosche et al.: Hippocampal volume as an index of Alzheimer neuropathology—Findings from the Nun Study, Neurology (2002); 58 pp. 1476-1482.

* cited by examiner

INTEGRATIVE PREDICTION OF A COGNITIVE EVOLUTION OF A SUBJECT

BACKGROUND OF THE INVENTION

Field of the Invention

The present disclosure is directed, in general, to imaging techniques for imaging biological tissues, and more specifically to the use of Magnetic Resonance Imaging (MRI) for measuring a cognitive evolution of a subject.

An aging population worldwide will stress the resources of public health systems. Dementia, including Alzheimer's disease (AD), affects around 10 million new people every year, and is one of the most prevalent old age diseases. One of its hallmarks is cognitive decline, where patients gradually lose their intellectual faculties due to the disease. However, due to disease and patient heterogeneity, prognosis (the forecast of future health trajectory as measured by clinical scores) is currently very difficult, and it is also not clear which patients would benefit from intervention. This makes caring for AD patients problematic and ineffective.

Predicting automatically and on an individual basis which patients are likely to stay cognitively healthy, and which are likely to be subject to cognitive decline, is a key component of more effective care for the individual patient and for healthcare systems in general, in particular in a resource-constrained environment. MRI is thereby likely to play an important role since cognitive decline is associated with atrophy, which can be nowadays robustly measured on a routine basis. However, there still exists a need for a tool which could predict an evolution of a cognitive function in order to help a physician to diagnose a disease.

SUMMARY OF THE INVENTION

The present invention proposes therefore a method and system for predicting an evolution of a cognitive score for a subject based on a measurement and a combination of biomarkers in order to help a physician to estimate a future evolution of a subject cognitive function as disclosed by the object of the independent claims. The present invention proposes to collect cognitive data for a subject and to determine a trend for the evolution of the cognitive function for said subject. Dependent claims describe further advantages of the invention.

In accordance with the invention there is provided a machine learning method for predicting the evolution of a cognitive score for a subject by automatically classifying a cognitive data set for said subject into either a first class associated with a first evolution of said cognitive score, or a second class associated with a second evolution of said cognitive score, wherein said first class corresponds to a first kind of evolution of a cognitive function (for instance a decline of the cognitive function) and said second class to a second kind of evolution of a cognitive function (for instance a non-decline). Of course, the machine learning method according to the invention is not limited to a two-class classification and the concept of the invention might be used for classifying a cognitive dataset into one class over N classes, with N>2. The predicted evolution of the score might be then used by a physician as additional information for a diagnosis of a cognitive disease like AD.

The cognitive set of data according to the invention is typically based on a combination of biomarkers such as normalized volumetric information, Cerebrospinal fluid (CSF) total tau (tTau), CSF Beta amyloid, APOEE4 genotype, and CDR sum-of-boxes (CDRSoB) neuropsychological score and comprises cognitive data for the considered biomarkers. Other biomarkers might be taken into account for the cognitive set of data if required. Advantageously, combining the "imaging biomarkers" (i.e. normalized volumetric information, typically volume measurements indicating atrophy of brain (sub-)structures with other biomarkers, like clinical scores and psychometric measures, increases the predictive power since complementary information is combined. The cognitive dataset might be stored in a database and automatically acquired by the system according to the invention in order to train a machine learning classification algorithm as explained below.

According to the claimed method, several cognitive datasets are determined for a group of subjects from cognitive data obtained or measured from the subjects of said group at a first time period T1, wherein a single or several cognitive datasets might be determined and analyzed by the system according to the invention for each subject. The cognitive datasets might be acquired and determined from cognitive data stored in a database of the system. The first time period T1 is typically defined as a month of a year.

The cognitive set of data comprises cognitive data, i.e. values for different biomarkers characterizing a subject, notably normalized volumetric information obtained for said subject and a first CDR sum-of-boxes (CDRSoB) neuropsychological score obtained for said subject at the first time period T1. According to the present invention, the normalized volumetric information is acquired, for each subject of the group of subjects, according to the following steps:
  acquiring brain structural images for each subject from said group of subjects and extracting for each subject volumetric information for a set of predefined brain regions;
  normalizing said volumetric information by the total intracranial volume of said subject in order to obtain for each subject said normalized volumetric information.

Each cognitive dataset may further comprise cognitive data representing a value or a measure of the following biomarkers:
  the Cerebrospinal fluid (CSF) total tau (tTau). The use of the CSF tTau advantageously increases the classification performance of the present method;
  the CSF Beta amyloid;
  the APOEE4 genotype.
Optionally, the cognitive dataset may comprise the age and sex of the subject.

The method according to the invention further comprises acquiring for each subject a second CDRSoB neuropsychological score, wherein said second CDRSoB neuropsychological score has been measured or obtained at a second time period T2 temporally situated after T1. The system according to the invention is in particular configured for automatically triggering the acquisition, of the second CDRSoB neuropsychological score after a predefined time period starting from b. For instance, it can prompt a physician to provide a second CDRSoB neuropsychological score for each subject after the lapse of the predefined time period which started from T1. Said predefined time period, which corresponds to a temporal gap between T1 and T2, is typically 18-42 months.

After acquisition of the second CDRSoB neuropsychological score for each subject, the method according to the invention comprises the following steps:
  automatically classifying each subject in function of the value of the second CDRSoB neuropsychological score compared to the value of the first CDRSoB neuropsychological score either into said first class or into said second class;

grouping the predefined brain regions within several atrophy networks (or groups), and determining for each subject said normalized volumetric information for each of said atrophy networks. There are preferentially three atrophy networks, respectively a neurological network comprising bilateral hippocampi and bilateral temporal lobe volumes, a functional approximation network comprising bilateral hippocampi and bilateral cingulate volumes, and a whole-brain network comprising all brain regions. Said grouping enables to use atrophy networks that are specific to a cognitive status which results in an increase of the performance of the overall prediction of the evolution of the cognitive score. Furthermore, the "functional approximation network" and "neurological network" offer increased interpretability by relying on very few brain regions;

training a two-class machine learning classification algorithm on the cognitive data sets of all subjects. Preferentially, for each subject, different cognitive datasets comprising each the normalized volumetric information for one of said several atrophy networks are created so that different cognitive datasets having each a different normalized volumetric information depending on the considered atrophy network are created for each subject and used as training datasets.

According to the present invention, the cognitive datasets are indeed used as learning datasets, wherein for each subject, each cognitive dataset is used as input of the algorithm and the obtained classification of the subject as output target of the algorithm, wherein the two-class machine learning classification algorithm is configured for classifying each cognitive data set, and therefore each subject, either in said first class or in said second class.

Finally, the claimed method proposes to use the trained two-class machine learning classification algorithm for classifying a new dataset for a subject. For this purpose, the method comprises, a prediction of the evolution of the cognitive score of a subject by using the trained two-class machine classification learning algorithm for automatically classifying the new cognitive dataset of said subject either into said first class or into said second class, wherein said new cognitive dataset is used as input of the trained two-class machine learning algorithm, and its output is then either the classification of the new cognitive dataset into said first class or into said second class.

Various disclosed embodiments include machine learning methods and corresponding systems for automatically predicting an evolution of the cognitive score of a subject through the acquisition of a cognitive dataset for said subject and using said cognitive dataset as input in the claimed trained two-class machine learning classification algorithm. The training of said algorithm is configured for defining a relationship between the set of cognitive data acquired for a subject and a future evolution of the cognitive score, wherein said evolution comprises two branches represented by the first class and the second class.

The foregoing has outlined rather broadly the features and technical advantages of the present disclosure so that those skilled in the art may better understand the detailed description that follows. In particular, the present invention may help a physician determining a future evolution of a cognitive function, like the evolution from mild cognitive impairment (MCI) to AD, or forecasting cognitive decline, notably from healthy controls enabling determining a cognitive dataset for a subject.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

For a more complete understanding of the present disclosure, and the advantages thereof, reference is now made to the following descriptions taken in conjunction with the accompanying drawings, wherein like numbers designate like objects, and in which:

Other features which are considered as characteristic for the invention are set forth in the appended claims.

Although the invention is illustrated and described herein as embodied in a integrative prediction of a cognitive evolution of a subject, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
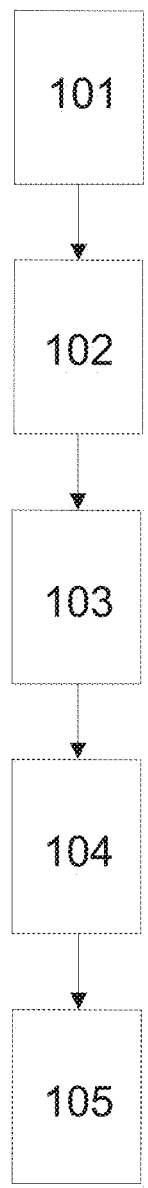
FIG. 1 illustrates a flowchart of a method for predicting the evolution of a cognitive score according to the invention.
Figure 2:
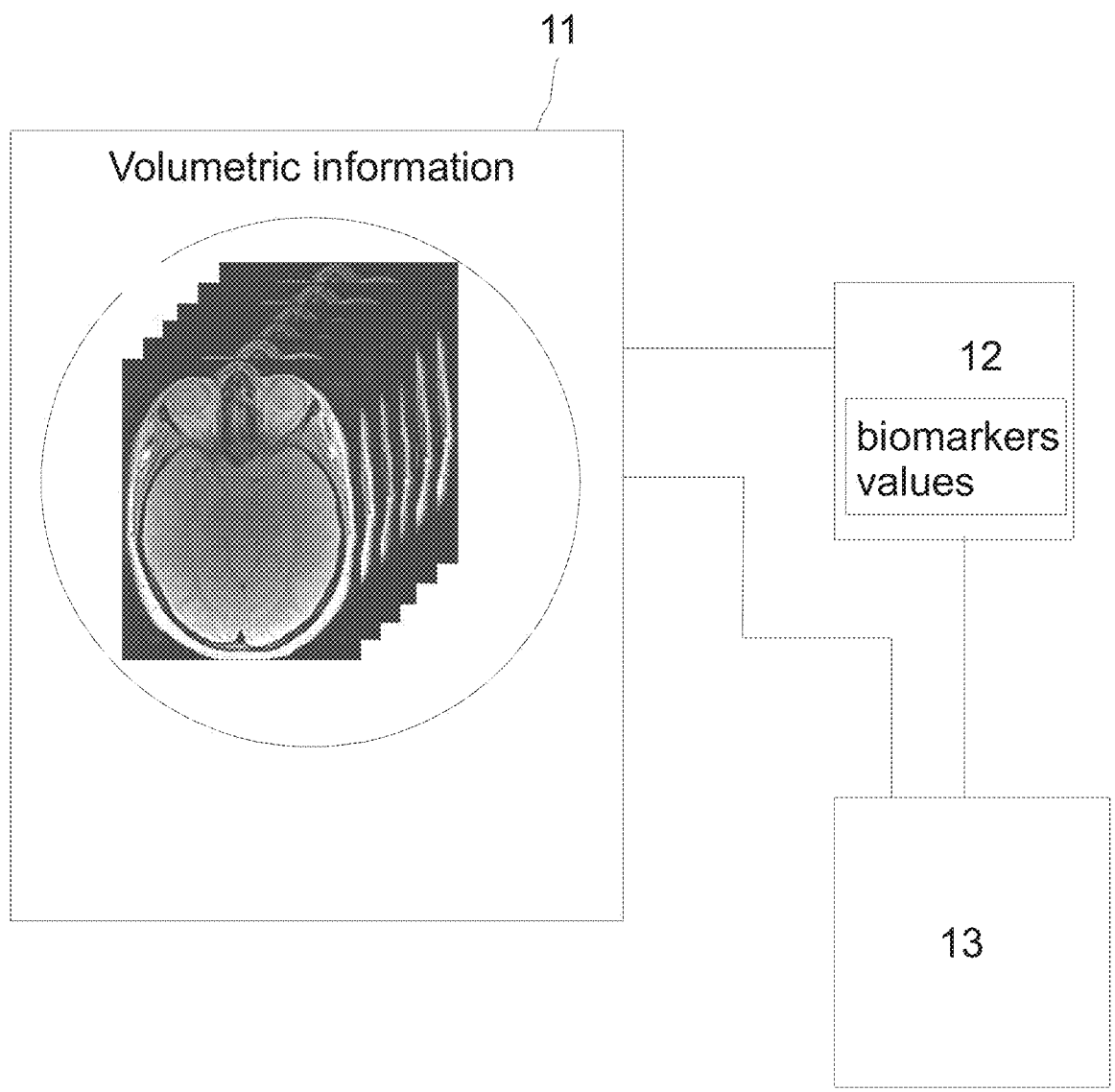
FIG. 2 illustrates a system for implementing the claimed method.

FIGS. 1 and 2, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

The present invention enables to predict an evolution of a cognitive score, or in other words, to evaluate or determine a trend within a future evolution of a cognitive function of a subject from a prior acquisition of cognitive data for said subject, wherein said cognitive data comprise values for biomarkers measured or obtained for said subject and grouped into cognitive dataset. The prediction obtained according to the present invention is based on a machine learning method 100 which requires the creation of learning datasets from a group of subjects.

For this purpose and as illustrated in FIGS. 1 and 2, for each subject of a group of subjects cognitive data are automatically collected by the system at step 101, for instance from a database 12, in order to create or determine cognitive datasets that will be used by the machine learning algorithm as training datasets. Said cognitive data comprise at least a normalized volumetric information and a CDRSoB neuropsychological score for each subject. Typically, a MRI apparatus 11 might be used for acquiring brain structural images from each subject of said group of subjects and extracting volumetric information for a predefined brain region, or preferentially, for a set of predefined brain regions, wherein the volumetric information is further normalized by the total intracranial volume of the subject. Preferentially, a set of 100 subjects is chosen and a set of 20-30, preferentially 27, predefined brain regions is defined. Step 101 further includes at least acquiring for each subject the value of a first CDRSoB neuropsychological score. Said value might be acquired from a database connected to the system according to the invention. Additionally, step 101 may further include acquiring for each subject at least one of the following cognitive data: a value of the CSF tTau, a value of the CSF Beta amyloid, the APOEE4 genotype, the age of the subject and optionally the sex of the subject. Said cognitive data are preferentially automatically acquired by the system and grouped into cognitive datasets for each subject. Preferentially, the cognitive data are characterized by a date indicating the time at which the cognitive data was measured or obtained. Preferentially, the system is able to automatically collect said date for each cognitive data in order to determine for each cognitive set of data and associate to the latter a time period, called first time period T1, which represents the time period at which the cognitive data of the cognitive dataset were measured or obtained.

At step 102, taking place after the first time period T1, the system according to the invention is configured for acquiring a second CDRSoB neuropsychological score for each subject. For instance, the system may automatically search in the database 12 for a second CDRSoB neuropsychological score characterized by a date of acquisition (i.e. the date at which said score was measured or obtained which is referred to hereafter as the second time period T2) which is separated from the first time period T1 by a predefined time period. The second CDRSoB neuropsychological score might be different from the first CDRSoB neuropsychological score obtained for the first time period T1. The difference between the score obtained for CDRSoB at T1 and T2, typically an increase or decrease of said score, is used for classifying the cognitive datasets, or in other words each subject, into one over two different classes, respectively a first class and a second class. For instance, in case of AD, the first class may correspond to an increase of said score at T2 with respect to T1 and might be labelled as "decliner", while the second class would correspond to a decrease or identical score and might be labelled as "non-decliner", since it is known that higher scores correspond to more impairment.

At step 103, predefined brain regions of said set of predefined brain regions might be automatically grouped together by a processing unit 13 of the claimed system in order to create atrophy networks, i.e. groups of regions that have biological relevance when considered together, wherein the normalized volumetric information is determined for each atrophy network of each subject. For instance, and in particular when considering AD, three different atrophy networks might be created for said predefined brain regions: a "neurological" network (bilateral hippocampi and bilateral temporal lobe volumes), a "functional approximation network" (bilateral hippocampi and bilateral cingulate volumes) and a "whole-brain network" (all brain regions). Advantageously, the grouping of predefined brain regions in the so-called atrophy networks enables to takes account of a spatial progression of the disease within the brain in function of the time (i.e. in function of the predefined time period separating T1 from T2) when training the machine learning classification algorithm on the training datasets. In other words, the grouping in atrophy networks improves the precision of the prediction according to the present invention by taking account of different temporal stages of a disease. Preferentially, for each atrophy network and each subject, a cognitive dataset comprising at least the normalized volumetric information for said atrophy network at T1 and the first CDRSoB neuropsychological score is created. In other words, there is for each subject a different cognitive dataset for each atrophy network, said different cognitive dataset comprising the normalized volumetric information for one of the atrophy networks. As already mentioned, said cognitive dataset may further comprise the value of the CSF tTau, the value of the CSF Beta amyloid, the APOEE4 genotype, the age of the subject and optionally the sex of the subject at the first time period T1.

At step 104, the processing unit 13 is configured for training a two-class machine learning classification algorithm on the cognitive datasets of all subjects, wherein for each subject, the cognitive dataset is the input to the two-class machine learning classification algorithm and the class in which said subject has been classified is the output target of said algorithm. The two-class machine learning classification algorithm uses in particular a random forest (e.g. R package random Forest) with 1001 trees, wherein parameters of the algorithm are learned from data, which involves repetitive random resampling of the data (also called bootstrapping) as well as random sampling of the features.

Preferentially, the processing unit 13 is configured for automatically up-sampling the cognitive datasets of the subjects belonging to the minority class among the first and second class by resampling with replacements from said minority class. Preferably, the processing unit is configured for automatically acquiring for each subject, for instance from the database 12, a complementary cognitive score for automatically classifying the subjects into complementary classes representing each an initial cognitive status of the subject at the first time period T1, for instance healthy, MCI, and AD, and for automatically up-sampling the minority complementary class in order to avoid bias of the two-class machine learning classification algorithm and improve its learning performance.

Preferentially, the processing unit 13 is configured for using a 10-fold cross-validation technique when training the two-class machine learning classification algorithm on the cognitive datasets. According to this technique, the cognitive datasets are split in 10 equal parts, wherein the algorithm is trained on 9/10 of the cognitive datasets, and its performance is evaluated on the 1/10 of the cognitive datasets which have not yet been used as input for said algorithm and are therefore used as "validation data". This is called one cross-validation "fold". The processing unit 13 is then configured for automatically rotating a partition of the cognitive datasets in order to use another 9/10 of the cognitive datasets (most of which will be in common with the first fold) for training purpose, and evaluate the algorithm on another 1/10 of the cognitive datasets (which has no overlap with the training data for this fold). Said procedure is automatically repeated by the processing unit eight more times until having used each of the 10 parts as validation data. Preferentially, the processing unit 13 is configured for automatically evaluating the performance of the two-class machine learning classification algorithm by repeating several times the whole procedure previously described, for instance 100 times (which means performing 100 times the 10-fold cross-validation, each time with different splits into training and validation sets) and automatically determining an accuracy of the obtained classification results. Preferentially, as long as said accuracy is below a predefined threshold, then the system according to the invention is configured for determining or acquiring additional cognitive datasets for further training the two-class machine learning classification algorithm until the obtained accuracy is above the predefined threshold.

At step 105, the system is configured for predicting the evolution of the cognitive score of a subject by using the trained two-class machine classification learning algorithm for automatically classifying a new cognitive dataset of said subject either into said first class or into said second class. In particular, the processing unit 13 is configured for authorizing step 105 only if the obtained accuracy is above the predefined threshold. This ensures obtaining accurate forecasting of the evolution of the cognitive score, i.e. accurate classifications of the cognitive datasets, and thus the subjects, either into the first class or into the second class.

The invention claimed is:

1. A machine learning method for predicting an evolution of a cognitive score for a subject by automatically classifying a cognitive dataset for said subject into either a first class associated with a first evolution of said cognitive score or a second class associated with a second evolution of said cognitive score, said cognitive set of data comprising biomarker cognitive data including normalized volumetric information and Clinical Dementia Rating sum-of-boxes (CDRSoB) neuropsychological score, the method comprising:
   a) determining the cognitive set of data for each subject of a group of subjects by acquiring biomarker cognitive data for the subject, wherein said biomarker cognitive data have been established or measured for said subject at a first time period T1, said acquisition of biomarker cognitive data comprising:
      acquiring brain structural images from said group of subjects and extracting for each subject volumetric information for a set of predefined brain regions;
      for each subject, normalizing said volumetric information by the total intracranial volume of said subject in order to obtain said normalized volumetric information;
      acquiring for each subject a first CDRSoB neuropsychological score;
   b) acquiring for each subject a second CDRSoB neuropsychological score, wherein said second CDRSoB neuropsychological score has been measured for the subject at a second time period T2 temporally situated after T1;
   c) automatically classifying each subject as a function of the value of the second CDRSoB neuropsychological score compared to the value of the first CDRSoB neuropsychological score either into said first class or into said second class;
   d) grouping the predefined brain regions within atrophy networks, and determining for each subject said normalized volumetric information for each of the atrophy networks;
   e) training a two-class machine learning classification algorithm on the cognitive data sets of all subjects, wherein for each subject there is a different cognitive dataset for each atrophy network, wherein for each subject, the cognitive data set is used as input of the algorithm and the obtained classification of the subject as output target of the algorithm, wherein the two-class machine learning classification algorithm is configured for classifying each cognitive data set either in said first class or in said second class;
   f) predicting the evolution of the cognitive score of a subject by using the trained two-class machine classification learning algorithm for automatically classifying a new cognitive dataset for said subject either into said first class or into said second class, wherein said new cognitive dataset is used as input of the trained two-class machine learning algorithm.

2. The method of claim 1, wherein there are three atrophy networks, respectively a neurological network comprising bilateral hippocampi and bilateral temporal lobe volumes, a functional approximation network comprising bilateral hippocampi and bilateral cingulate volumes, and a whole-brain network comprising all brain regions.

3. The method of claim 1, wherein a subject is classified into the first class if the value of the second CDRSoB neuropsychological score increased compared to the value of the first CDRSoB neuropsychological score, and a subject is classified into the second class otherwise.

4. The method according to claim 1, wherein the two-class machine learning classification algorithm is a random decision forest algorithm with 1001 trees.

5. The method according to claim 1, wherein parameters of the two-class machine learning classification algorithm are learned from data, which involves repetitive random resampling of the cognitive datasets.

6. The method according to claim 5, comprising up-sampling the minority class among the first class and the second class by resampling with replacement from the minority class.

7. The method according to claim 5, comprising up-sampling the cognitive datasets belonging to a complementary class representing a minority class for an initial cognitive status of the subject.

8. The method according to claim 1, comprising using a 10-fold cross-validation technique.

9. The method according to claim 1, wherein the acquired biomarker cognitive data for the determination of the cognitive set of data further comprise at least one of the following cognitive data: the Cerebrospinal fluid (CSF) total tau (tTau), the CSF Beta amyloid, and the APOEE4 genotype.

10. The method according to claim 1, wherein the cognitive dataset comprises additionally the age and sex of the subject.

11. A system for predicting an evolution of a cognitive score for a subject by automatically classifying a cognitive data set for said subject into either a first class associated with a first evolution of said cognitive score or a second class associated with a second evolution of said cognitive score, said cognitive set of data comprising biomarker cognitive data including normalized volumetric information and Clinical Dementia Rating sum-of-boxes (CDRSoB) neuropsychological score, the system comprising:
   a magnetic resonance imaging (MRI) apparatus configured for acquiring brain structural images for a subject and extracting for said subject volumetric information for a set of predefined brain regions;
   a database for storing cognitive data for the cognitive datasets;
   a processing unit for collecting from the MRI apparatus and/or within said database cognitive data for determining the cognitive datasets, said processing unit being configured for training a two-class machine learning classification algorithm on the determined cognitive datasets;

wherein the system according to the invention is configured for performing the steps of the method according to claim 1.

\* \* \* \* \*